United States Patent [19]

Rosenberg et al.

[11] Patent Number: 5,840,547
[45] Date of Patent: Nov. 24, 1998

[54] BIOEMULSIFIERS

[75] Inventors: Eugene Rosenberg, Givat Shmuel; Eliora Z. Ron, Tel-Aviv, both of Israel

[73] Assignee: RAMOT University Authority for Applied Research & Indfustrial Development Ltd., Tel-Aviv, Israel

[21] Appl. No.: 702,711

[22] PCT Filed: Jan. 5, 1996

[86] PCT No.: PCT/US96/00168

§ 371 Date: Sep. 30, 1996

§ 102(e) Date: Sep. 30, 1996

[87] PCT Pub. No.: WO96/20611

PCT Pub. Date: Jul. 11, 1996

[30] Foreign Application Priority Data

Jan. 5, 1995 [IL] Israel ........................................ 112254

[51] Int. Cl.[6] ............................. A23L 1/05; A61K 9/107; B01F 17/30; C07K 14/22

[52] U.S. Cl. .................... 435/71.2; 106/501.1; 252/8.81; 252/356; 424/70.21; 424/401; 426/654; 435/252.1; 504/117; 514/773; 514/938

[58] Field of Search ................................. 252/8.81, 8.91, 252/356; 424/400, 401, 70.19, 70.21; 426/580, 582, 583, 654; 435/71.2, 252.1; 514/773, 938, 939; 530/300, 322, 359, 395, 825; 504/116, 117, 124; 119/650, 651; 106/501.1; 510/463, 499, 535

[56] References Cited

U.S. PATENT DOCUMENTS 4,380,504 4/1983 Gutnick et al. ........................ 252/356
4,870,010 9/1989 Hayes ...................................... 514/852
4,883,757 11/1989 Gutnick et al. ...................... 435/252.1
4,943,390 7/1990 Hayes et al. ............................ 252/355

OTHER PUBLICATIONS

Kaempfer, et al., *Numerical Classification and Identification of Acinetobacter Genonmic Species* (Abstract). Biosciences Information Service, Philadelphia, Pa (1993).

Journal of Applied Bacteriology, vol. 75, No. 3, 1993, pp. 259–268.

Navon–Venezia et al., Alasan, a New Bioemulsifier From *Acinetobacter radioresistens*, Applied and Enviormental Microbiology,Sept. 1995, vol. 61, No. 9. pp. 3240–3244.

Nishimura et al., *Acinetobacter radioresistens* Sp. Nov. Isolated from Cotton and Soil, International Journal Of Systematic Bacteriology, Apr. 1988, vol. 38, No. 2, pp. 209–11.

Chemical Abstracts, vol. 121, No. 15, Oct. 10, 1994, p. 995, 17864f, Juwarker et al., "Hydrocarbon Partitioning in Soil Slurries by Biosurfactant from Acinetobactor radioresistens" *J. Microb. Biotechnol.*, 1993.

*Primary Examiner*—Jeffrey E. Russel
*Attorney, Agent, or Firm*—William H. Dippert; Cowan, Liebowitz & Latman, P.C.

[57] ABSTRACT

A bioemulsifier designated Alasan or E-KA53 is produced from *Acinetobacter radioresistens* strain KA53. In its essentially pure form it has the characteristics of a molecular weight of from about 100,000 to 2,000,000 Daltons; emulsifying activity which increases with preheating at increasing temperatures—60°–90° C.; resistance to strong alkali while retaining increased emulsifying activity; reduced viscosity that varies as a function of temperature treatment; and emulsifying activity that varies as a function of pH and magnesium ions.

30 Claims, 1 Drawing Sheet

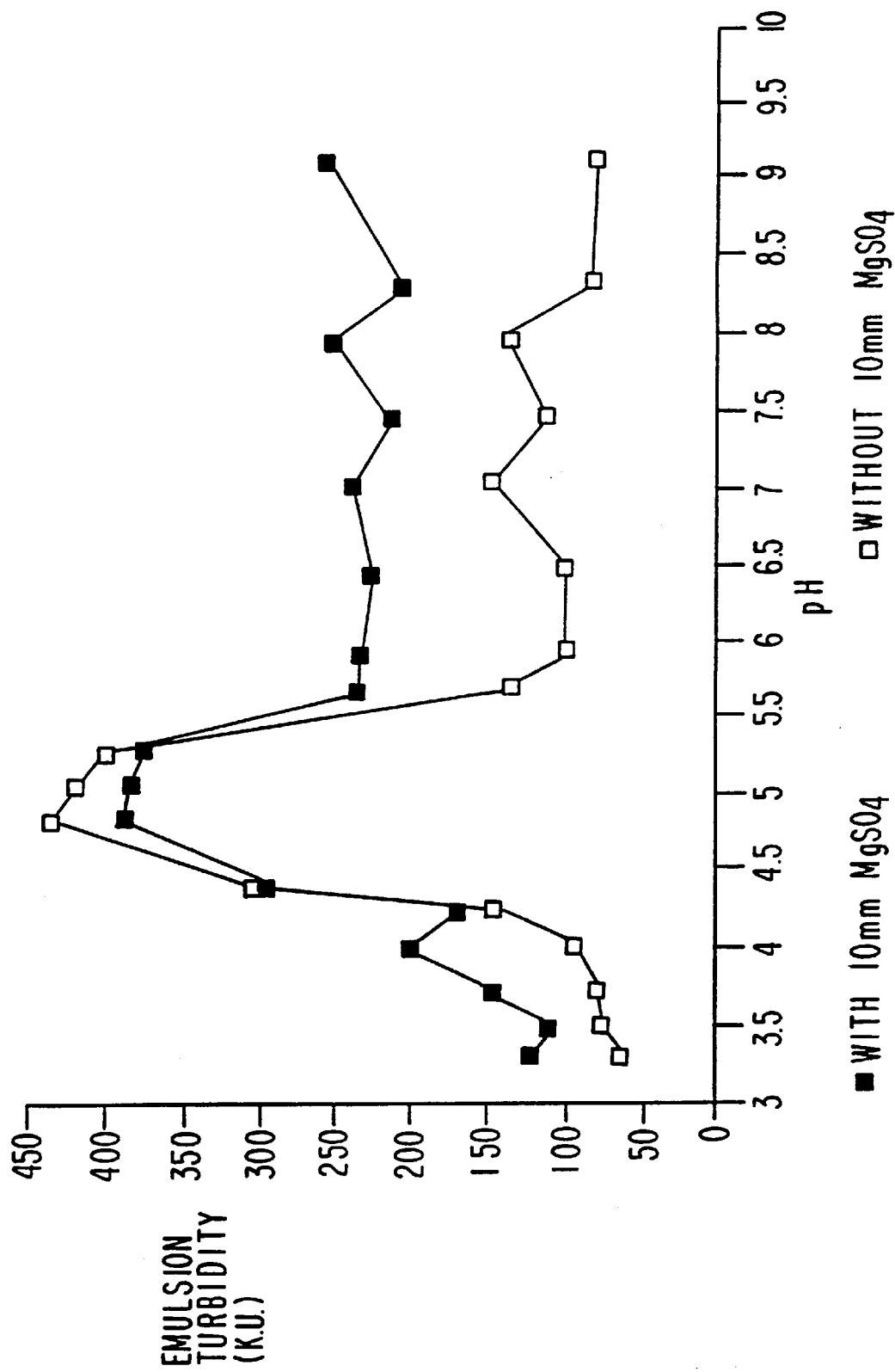

BIOEMULSIFIERS

FIELD OF INVENTION

The present invention relates to polymeric substances produced by bacteria, which are used as emulsifying agents. The present invention more particularly relates to bioemulsifiers produced by bacteria, for use in detergents, cosmetics, agriculture, medicine, the food industry, the pharmaceutical industry, the textile industry, and for bioremediation.

BACKGROUND OF INVENTION

Bioemulsifiers are surface-active agents derived from biological sources such as bacteria, yeast and fungi, that contain both hydrophobic and hydrophilic groups. The hydrophobic groups tend to be expelled by the water, while the polar or hydrophilic groups tend to remain in the water. The hydrophobic moiety is usually a hydrocarbon chain of a fatty acid, whereas the hydrophilic part is usually alcohol groups of sugars, carboxyl groups of uronic acids, amino acids or fatty acids, and phosphate-containing portions of phospholipids. The surface active properties of an emulsifier molecule depend on the balance between the hydrophobic and hydrophilic portions.

Bioemulsifiers can be classified into two main groups: (i) Low molecular weight lipid-containing such as glycolipids, fatty acids, phospholipids and lipopeptides and (ii) high molecular weight amphipathic molecules. High molecular weight emulsifiers are amphipathic molecules, containing both hydrophilic and hydrophobic moieties. Their structure enables them to be efficient stabilizers of hydrocarbon-in-water emulsions.

These biopolymers usually consist of a combination of a hydrophilic polysaccharide backbone with additional hydrophobic components that may be covalently or non-covalently linked. The hydrophobic moiety necessary for emulsifications, can be protein as in the *Acinetobacter calcoaceticus* BD4 emulsifier and liposan from *Candida lipolytica*, or a lipid as in the RAG-1 emulsan of *A. calcoaceticus* RAG-1.

Two extracellular polysaccharide-containing emulsifiers, produced by *A. calcoaceticus*, have been studied extensively: RAG-1 and BD4 emulsans. The RAG-1 emulsan is a non-covalently linked complex of a lipoheteropolysaccharide and protein. The polysaccharide, called apoemulsan, has a molecular weight of about $9.9 \times 10^5$. The major sugar components of apoemulsan are D-galactosamine, D-galactosaminuronic acid and diaminodideoxy glucosamine. Fatty acids are covalently linked to the polysaccharide backbone through O-ester and N-acyl linkages.

The fatty acids constitute about 5–15% (w/w) of the polymer and contribute to the amphipathic behavior of emulsan. RAG-1 emulsan stabilizes emulsions by binding tightly to the hydrocarbon-water interface, forming a strong polymeric film. The anionic heteropolysaccharide binds considerable amount of water and, together with the strong negative surface charge, prevents coalescence of the droplets. With RAG-1 emulsan, the protein is not absolutely required for emulsifying activity, probably because of the hydrophobic fatty acids that contribute significantly to its activity.

*A. calcoaceticus* BD4 produces a large polysaccharide capsule. When released into the medium, the capsular polysaccharide forms a complex with proteins which then becomes an effective emulsifier. Thus, the protein portion plays a crucial role in the emulsifying activity of the emulsan. The BD4 emulsan polysaccharide (PS-4) consists of the repeating heptasacccharide unit: L-rhamnose, D-glucose, D-glucuronic acid and D-mannose in molar ratios of 4:1:1:1. Extracellular protein fractions of BD4, free of polysaccharide or the polysaccharide by itself, were not active. However, reconstitution of the two portions together showed the original emulsifying ability.

Emulsifiers are used widely in industry, e.g., in medical and cosmetic products and in food systems. They can be used as agents to combat oil spills on beaches and in the sea. The materials that are currently in use commercially as emulsifiers are produced mainly by chemical synthesis. There is a great interest in studying bioemulsifiers because they have some advantages, such as their selectivity for specific interfaces, generally low toxicity and biodegradability. The enormous diversity of microbial emulsifiers provides a rich source to find new agents which possess the right combination of properties for specific applications.

SUMMARY OF INVENTION

E-KA53, also called Alasan, is a new emulsifier produced by *Acinetobacter radioresistens* strain KA53. The strain was isolated from an oil polluted sample taken near a gas station according to the standard enrichment culture technique for Acinetobacter, using sodium acetate as the carbon source. The strain was identified as Acinetobacter by physiological and genetic studies: colonies of KA53 contained nonmotile, oxidase-negative coccobacilli, and its DNA transformed an *Acinetobacter calcoaceticus* BD413 trp E27 strain to prototrophy. Alasan is new and different from previously studied Acinetobacter emulsans in that it contains covalently linked alanine and was extremely stable to heat and alkali conditions. The new bioemulsifier Alasan has a strong emulsifier activity to a wide variety of organic and biological materials.

The bioemulsifying activity is increased by preheating, reaching a maximum after treatment at about 90° C., even in the presence of 0.1N sodium hydroxide, and has potential wide applicability for use in detergents, cosmetics, medicine, the food industry, the pharmaceutical industry, the textile industry, bioremediation and in agriculture, for example, with pesticide and herbicide formulations. In general, Alasan has potential uses in any formulation that involves oil-in-water emulsions, and suspensions of hydrophobic substances such as herbicides or pigments.

BRIEF DESCRIPTION OF THE DRAWINGS

The FIGURE represents a plot reflecting the effect of pH and magnesium ions on the emulsifying activity of an embodiment of the invention.

DETAILED DESCRIPTION OF THE INVENTION

The bioemulsifiers E-KA53 or APO-E-KA53 of the present invention have the following physical, chemical and emulsifying properties:

Molecular Weight: about 100,000 to 2,000,000 Daltons.

Stability to 100° C. (see Table 2).

Emulsifying activity which increases with pretreatment at increasing temperature (see Table 3).

Resistance to strong alkali while retaining increased emulsifying activity (see Table 2).

Reduced viscosity which varies as a function of temperature (see Table 3).

Emulsifying activity that varies as a function of pH and magnesium ions (see the FIGURE).

The amino acid and carbohydrate building blocks of E-KA53 after most of the protein is removed (hereafter designated APO-E-KA53) are as shown in Tables 4 and 5.

Alanine represents 7 percent of the total dry weight of APO-E-KA53 (see Table 4).

Acid-base titration of APO-E-KA53 showed it to be an anionic polymer containing 1.28 micromoles of acid per mg.

The UV absorption spectrum of APO-E-KA53 showed a single maximum at 209 nm, probably due to the N-acyl group of amino sugars or the amide linkage of alanine in the polymer.

The $C_{13}$-NMR of APO-E-KA53 is summarized in Table 6. The growth characteristics and emulsifier production during a batch fed fermentation run are summarized in Table 7 below. Ethanol, urea, $MgSO_4$ and trace elements were added to the EM medium as required (footnote, Table 7). Strain KA53 had an approximate doubling time of 2.4 hr during the initial 20 hr. exponential phase of growth. Between 24–72 hr., the turbidity increased linearly. At the conclusion of the experiment, 87 hr., maximum A600 of 33 was reached. Between 43–87 hr., the ratio of cell biomass (mg/ml) to A600 was approx. 0.63. The viable count (data not shown) decreased slowly after reaching a maximum of $8.0 \times 10^9$ cells/ml at 68 hr. The pH of the medium increased from 7.0 to 8.2 during the initial 38 hr. and remained relatively constant. The total biomass at the end of the fermentation was 23.6 g/l. The total emulsifying activity (cell bound plus extracellular) increased throughout the experiment, reaching 220 U/ml after 87 hr. The ratio of emulsifying activity (U/ml) to cell biomass (g/l) increased from 4.9 at 20 hr. (exponential phase) to 7.3 at 64 hr. and 11.6 at 87 hr. Assay of cell-free supernatant fluids (Table 6) showed that most of the emulsifying activity was extracellular. The maximum value of the extracellular activity reached 190 U/ml after 87 hr. of growth, representing 87% of the total emulsifying activity.

The following standard emulsification assay was used to measure total emulsifying activity, and extracellular emulsifying activity during growth:

Samples to be tested (0.1–0.5 ml) were introduced into a 125 ml flask containing TM buffer (20 mM Tris HCl buffer, pH 7.0 and 10 mM $MgSO_4$) to a final volume of 7.5 ml and then 0.1 ml mixture (1:1, vol/vol) of hexadecane (Merck) and 2-methylnaphthalene (Fluka) was added. The assay mixture was incubated at 30° C. with reciprocal shaking (160 strokes/min) for 1 hr. Turbidity was then determined in a Klett-Summerson photometer (green filter). One unit of emulsifying activity per milliliter is defined as that concentration of activity that yields 100 Klett units (K.U.) in the assay mixture.

Ammonium Sulfate Precipitation of the KA53 Emulsifier

After 87 hr. of growth in the fermentor (Table 7) the whole broth (1230 ml) was collected and centrifuged to yield 1120 ml of crude supernatant fluid. The supernatant was filtered through 0.45 μg filter and concentrated by ammonium sulfate into two fractions, 0–65% and 65–70% saturation. Seventy nine percent of the activity was recovered in the 0–65% and 25% in the 65–75% fraction. The 0–65% (2.35 g) fraction had a specific activity of 227 U/mg. It is referred to as E-KA53.

Emulsification of pure hydrocarbon.

Alkane hydrocarbons ranging from pentane ($C_5$) to octadecane ($C_{18}$) were assayed for their ability to serve as substances for emulsification (Table 8). The higher the molecular weight of the alkane, the better was the emulsion formed. Pentane, hexane, cyclohexane, heptane and iso-octane were not emulsified effectively, whereas $C_{10}$ to $C_{18}$ compounds were emulsified effectively.

Benzene, alklybenzenes and 2-methylnaphthalene were assayed for their ability to be emulsified by E-KA53, as set forth in Table 8 below. Benzene was not emulsified. However, benzene derivatives containing methyl groups, i.e., toluene and the xylenes were emulsified slightly. 2-methylnaphthalene was clearly a better substrate than the methyl benzenes. The two odd-chain alkylbenzenes tested, o-propylbenzene and heptylbenzene, were better substrates than the four even-chain alkylbenzenes tested. Maximum emulsifying activity was obtained with heptylbenzene.

Emulsification of hydrocarbon mixture. (Table 8).

Mixtures containing aromatic compound and an aliphatic hydrocarbon such as hexadecane and 2-methylnaphthalene were excellent substrates for E-KA53 emulsification. At a ratio of 2 vol 2-methylnaphthalene, to 1 vol hexadecane, the emulsion turbidity was 1400 K.U. compared to 950 K.U. for a 1:1 mixture and less than 600 K.U. for each of the pure hydrocarbons. The ability of E-KA53 to excellently emulsify crude oil, vegetable oil and coconut oil was observed.

The isolation of the novel strain KA53 from which the bioemulsifier KA53 has been isolated, is described in Example 1. This strain was deposited with the National Collections of Industrial and Marine Bacteria Ltd (NCIMB), Aberdeen, Scotland. Pursuant to the provisions of the Budapest Treaty on the International Recognition of the Deposit of Microorganisms for the purpose of the Patent procedure on 9th Nov. 1994, under Accession Number NCIMB 40692.

EXAMPLE 1

Acinetobacter KA53 was isolated by the enrichment culture technique, using acetate as the carbon energy source. Using standard enrichment culture techniques for the isolation of Acinetobacter, 12 different strains were isolated from oil polluted soil samples taken near a gas station. The strains were grown to stationary phase in EM medium (see Table 7 for medium composition), centrifuged and the extracellular fluids screened for emulsifying activity, using the standard emulsification assay. The strain that yielded the highest emulsification value, referred to as KA53, was chosen for further study. Strain KA53 was identified as *Acinetobacter radioresistens* by physiological and genetic characterization. The cells are aerobic, nonmotile short gram-negative rods that become more coccoid in the stationary phase. They are oxidase-negative and catalase positive. DNA derived from KA53 was able to transform the competent auxotrophic *A. calcoaceticus* strain BD4 to prototrophy. India ink staining indicated that the exponentially growing cells had a minicapsule. The strain grew on ethanol, proline, DL-4-aminobutyrate, glutarate, malonate, azelate, DL-lactate, phenylactate, L-phenylalanine and acetate as the carbon source, but failed to grow on trans-aconitate, citrate, aspartate, β-alanine, L-histidine, D-malate, histamine, glucose, sucrose, serine or tryptophan. Strain KA53 was not sensitive to BD4-specific or RAG-1-specific bacteriophages. Strain KA53 did not hydrolyze gelatin and grew on EM agar at 37° C. and 41° C., but not at 44° C.

EXAMPLE 2

Growth of E-KA53 and Production of E-KA53

Growth and emulsifier production experiments were carried out in ethanol medium (EM) that contained per liter of deionized water: 0.5% ethanol (v/v), as a carbon source, 1.8 g urea, 13.7 g of $Na_2HPO_4$, 7.2 g $KH_2PO_4$. 0.4 g $MgSO_4 \cdot 7H_2O$ and 1 ml of trace elements solution.

Trace elements solution contained (per 10 ml) 3.68 mg of $CaCl_2 \cdot 2H_2O$, 6.24 mg of $CuSO_4 \cdot 5H_2O$, 6.04 mg $FeSO_4 \cdot 7H_2O$, 5.94 $MnSO_4 \cdot 4H_2O$, 4.22 mg $ZnSO_4 \cdot 7H_2O$, 7.88 $CoCl_2.6H_2O$ and 6.96 mg $Na_2MoO_4$. Additional nutrients were added during the fermentation as described in Table 7.

Growth and emulsifier production were carried out in a 2.5 liter fermentor (Multigen, New Brunswick Scientific Co. Inc.) equipped with an oxygen electrode containing 1.4 liter EM medium at 30° C. The rate of aeration and stirring was regulated manually according to the rate of oxygen uptake. The initial conditions were: aeration of 1.0 lpm and stirring rate of 200 rpm. The final conditions were: aeration of 2.5 lpm and stirring rate of 550 rpm.

The strain was maintained on Brain Heart Infusion (BHI) and agar (3.7% BHI solidified with 2% agar, both from Difco). After incubation at 30° C. for 3 days, the plates were stored at 4° C. Transfers were performed monthly.

Bacterial Growth

Bacterial growth was initiated by introducing a 0.1% inoculum obtained from a starter culture that was grown in 5 ml of EM medium in a 125 ml flask at 30° C. for 24 h. Bacterial growth was followed by determining turbidity in a Klett-Summerson photometer (green filter), or absorbance in a Gilford spectrophotometer (600 nm) and by determining viable counts by plating an appropriate dilution on BHI agar.

EXAMPLE 3

The cell-free supernatant fluid (1 liter) was brought to 65% ammonium sulfate saturation by addition of 430 g salt with stirring at 40° C. It was then left overnight in the cold with stirring. The turbid suspension was centrifuged to 4° C. at 10,000×g for 10 min and the pellets were resuspended in deionized water and dialyzed extensively in the cold and then lyophilized. The dried material that precipitated at 65% saturation of salt, was termed E-KA53.

EXAMPLE 4

The ability of alasan to stabilize highly dispersed oil-in-water emulsions was further demonstrated. Mixtures containing 160 mg liquid paraffin oil or 180 mg Soybean oil and 0.5 mg alasan or 0.5 mg of the deproteinized apo-alasan in 10 ml of 30 mM Tris-Mg buffer, pH 7.2, were emulsified by ultrasonication. Turbidities were determined immediately (t=0) and after standing 1, 6 and 10 days. The results are set forth in the following table:

TABLE 1

Stabilization of Light Paraffin and Soybean Oil-in-Water Emulsions with Alasan

| Oil | Emulsifier | Turbidity (K.U.) at | | | |
|---|---|---|---|---|---|
| | | t = 0 | 1 d | 6 d | 10 d |
| Liquid paraffin | None | 3,700 | 30 | 0 | 0 |
| Liquid paraffin | Alasan | 11,600 | 8,200 | 4,300 | 4,000 |
| Liquid paraffin | Apo-alasan | 8,600 | 6,500 | 3,200 | 2,700 |
| Soybean | None | 7,200 | 70 | 0 | 0 |
| Soybean | Alasan | 10,500 | 9,000 | 8,950 | 8,900 |
| Soybean | Apo-alasan | 9,400 | 7,700 | 7,100 | 6,700 |

Emulsions of liquid paraffin and soybean oils, prepared by ultrasonication in the absence of an emulsifier, broke in a few hours, leaving less than 1% of the oil dispersed in the aqueous phase. On the other hand, emulsions prepared in the presence of 0.005% alasan were stable for at least 10 days. The partial drop in turbidity was due exclusively to creaming and not coalescence of oil drops, because gentle hand mixing resulted in obtaining the initial turbidity. The deproteinized preparation of the emulsifier, apo-alasan, was almost as effective as alasan. Alasan was also effective in stabilizing emulsions prepared with food grade vegetable and coconut oils.

EXAMPLE 5

Samples of the filtered supernatant fluid following growth of strain KA53 on EM medium were heated for different times at 100° C., either at neutral pH or in 0.1N NaOH. After the alkali treatment, the sample was neutralized to pH 7. Samples were assayed for emulsifying activity before and after overnight dialysis. (Molecular weight cutoff 6–8 kDa.)

TABLE 2

Effect of Heat and Alkali Treatment on the Emulsifying Activity of Alasan

| Treatment at 100° C. (min) | Emulsifying activity (U/ml) | | Relative activity[a] |
|---|---|---|---|
| | Before dialysis | After dialysis | |
| 0 | 600 | 585 | 1.0 |
| at pH 7 | | | |
| 10 | 1350 | 1730 | 2.3 |
| 15 | 1500 | 1340 | 2.5 |
| 45 | 1140 | 980 | 1.9 |
| 60 | 1500 | 1340 | 2.5 |
| in 0.1N NaOH | | | |
| 2 | 1260 | 680 | 2.1 |
| 5 | 1710 | 620 | 2.9 |
| 10 | 1530 | 510 | 2.6 |
| 15 | 1530 | 650 | 2.6 |
| 30 | 1800 | 260 | 3.0 |
| 45 | 1370 | 83 | 2.3 |
| 60 | 1080 | 45 | 1.8 |

[a]Relative activity is the activity after heat treatment compared to the untreated control (none of the samples dialyzed).

EXAMPLE 6

Five milliliter solutions of 2 mg/ml of E-KA53 and apo-KA53 in 20 mM Tris buffer, pH 7.0, were placed in a thermoblock and incubated for 10 min at 30° C. After removal of 1.8 ml samples for measuring viscosity and 0.1 ml samples for measuring emulsifying activity, the solutions were then heated at the next highest temperatures for 10 min. This procedure was repeated up to 100° C. After each heat treatment the samples were cooled and viscosity and emulsifying activity measured at 30° C.

TABLE 3

The Effect of Temperature Treatment on the Viscosity and Emulsifying Activity of E-KA53 and APO-KA53

| | E-KA53 | | APO-KA53 | |
|---|---|---|---|---|
| °C. | Reduced viscosity (cm$^3$/g) | Sp. emulsif. activity (U/mg) | Reduced viscosity (cm$^3$/g) | Sp. emulsif. activity (U/mg) |
| 30 | 240 | 90 | 389 | 27 |
| 40 | 510 | 95 | 400 | 35 |
| 50 | 680 | 90 | 341 | 48 |
| 60 | 505 | 190 | 341 | 43 |
| 70 | 215 | 325 | 343 | 55 |
| 80 | 160 | 425 | 329 | 38 |
| 90 | 150 | 520 | 335 | 40 |
| 100 | 120 | 270 | 278 | 45 |

EXAMPLE 7

Amino acid analysis was carried out on 10 μg of each sample following hydrolysis at 100° C. in 6N HCl for 24 hr.

The sensitivity of the detection was 0.3%. The results were as follows:

TABLE 4

Amino Acid Analysis of Alasan and Apo-alasan

| Amino acid | Content (wt %) Alasan | Apo-alasan |
|---|---|---|
| Ala | 4.5 | 7.0 |
| Arg | 0.6 | 0.2 |
| Asp | 2.5 | 0.5 |
| Glu | 2.1 | 1.1 |
| Gly | 1.3 | 1.2 |
| His | 0.4 | N.D.[a] |
| Ileu | 0.1 | 0.3 |
| Leu | 1.3 | 0.3 |
| Lys | 2.5 | 0.3 |
| Met | 0.1 | N.D. |
| Phe | 0.8 | 0.2 |
| Pro | 0.4 | 0.4 |
| Ser | N.D. | 0.5 |
| Thr | 1.4 | 0.3 |
| Tyr | 1.0 | 0.5 |
| Val | 1.6 | 0.4 |

[a]N.D., not detected.

EXAMPLE 8

Chromatography and staining of sugars and amino acids were performed. The solvent system was ethyl acetate, pyridine, water, acetic acid (5:5:3:1, by vol). The results are set forth in the following table:

TABLE 5

Thin-layer Chromatography of Acid-hydrolyzed APO-E-KA53

| | | Reaction | | |
|---|---|---|---|---|
| | Rf | ninhydrin | AgNO3 | Identification |
| Time of hydrolysis in 4N HCl | | | | |
| 1 hr | 0.07 | + | + | Unknown |
| | 0.44 | − | + | Galactoses |
| | 0.49 | − | + | Glucose |
| 4 hr | 0.07 | + | + | Unknown |
| | 0.25 | + | − | Alanine |
| | 0.31 | + | + | Galactosamine |
| | 0.38 | + | + | Glucosamine |
| 20 hr | 0.07 | + | + | Unknown |
| | 0.25 | + | − | Alanine |
| | 0.32 | + | + | Galactosamine |
| | 0.37 | + | + | Glucosamine |
| Standards: | | | | |
| Glucuronic acid | 0.22 | − | + | |
| Alanine | 0.25 | + | − | |
| Galactosamine | 0.32 | + | + | |
| Glucosamine | 0.37 | + | + | |
| Galactosamine | 0.44 | − | + | |
| Valine | 0.47 | + | − | |
| Glucose | 0.49 | − | + | |

EXAMPLE 9

Spectra of APO-E-KA53 (50 mg in 0.5 ml $D_2O$) was recorded at 25° C. TMS was used as external standard. The results were as follows:

TABLE 6

Tabulated $^{13}$C-NMR Data

| Tentative atoms | Signal (ppm) |
|---|---|
| Carbonyl atoms | 177.67, 176.54, 174.33, 174.98, 173.29, 167.78 |
| Anomeric atoms | 102.60, 101.06, 97.06, 96.77, 96.22, 95.01 |
| Sec. alcohols or O-substituted Primary & sec. alcohols | 76.58, 87.98, 74.01, 72.88, 71.93, 71.66, 71.22, 70.45, 69.31, 68.11, 67.35, 66.05 |
| Primary alcohols | 62.84, 60.57 |
| $C_2$ of amino sugars | 57.61, 55.79, 53.56, 49.50, 45.87, 44.41, 42.80 |
| CH of alanine | 50.41 |
| Unidentified | 32.48, 31.59 |
| Methyl groups | 25.50, 21.90, 21.20, 17.41, 16.44, 14.80 |

EXAMPLE 10

Strain KA53 was grown in a 2.5 liter fermentor containing 1.4 liter EM medium (5 ml ethanol, 1.8 g urea) 27.4 g of $Na_2HPO_4$, 14.52 g $KH_2PO_4$, 0.8 g $MgSO_4.7H_2O$ and 1 ml of trace elements solution per liter of deionized water; the trace elements solution contained (per 10 ml) 3.68 mg of $CaCl_2.2H_2O$, 6.24 mg of $CuSO_4.5H_2O$, 6.04 mg $FeSO_4.7H_2O$, 5.94 $MnSO_4.4H_2O$, 4.22 mg $ZnSO_4.7H_2O$, 7.88 $CoCl_2.6H_2O$ and 6.96 mg $Na_2MoO_4$. The growth and emulsifier production was as follows:

TABLE 7

Growth and Emulsifier Production by Strain KA53

| Time (hr) | pH | Turbidity $A_{600}$ | Dry weight (mg/ml) Cells | Extracellular | Emulsifying Activity (U/ml) Total | Extracellular |
|---|---|---|---|---|---|---|
| 0 | 7.0 | 0.01 | N.D. | N.D. | <5 | <5 |
| 20[a] | 7.2 | 5.38 | N.D. | 0.60 | 30 | 19 |
| 24[b] | 7.3 | 12.2 | 6.7 | 0.63 | 35 | 11 |
| 38[c] | 8.2 | 15.5 | 13.7 | 1.10 | 47 | 35 |
| 43 | 8.1 | 19.6 | 13.9 | 1.60 | 87 | 65 |
| 48[d] | 8.2 | 23.0 | 14.6 | 2.33 | 90 | 70 |
| 64[e] | 7.8 | 26.2 | 16.5 | 2.53 | 120 | 98 |
| 68[b] | 7.9 | 30.7 | 19.0 | 2.90 | 170 | 170 |
| 72[b] | 8.1 | 32.1 | 19.0 | 3.25 | 180 | 150 |
| 87 | 8.3 | 33.0 | 19.0 | 4.60 | 220 | 190 |

[a]0.5% ethanol and 0.18% urea
[b]1.0% ethanol
[c]1.0% ethanol, 0.18% urea, 0.04% $MgSO_4.7H_2O$ and 0.1% trace elements (TE)
[d]0.5% ethanol
[e]0.5% ethanol, 0.18% urea and 0.1% TE

EXAMPLE 11

The standard emulsification assay was used with 0.1 mg/ml of Alasan and 0.1 ml of the indicated hydrocarbon substrates, to measure hydrocarbon substrate specificity. The results are set forth in the following table:

TABLE 8

Hydrocarbon Substrate Specificity of Alasan

| Hydrocarbon substrate | Emulsion turbidity (K.U.) |
|---|---|
| Alkanes | |
| n-Pentane | <20 |
| n-Hexane | 27 |
| Cyclohexane | <20 |
| n-Heptane | 43 |
| iso-Octane | 24 |
| Decane | 240 |
| Tetradecane | 290 |
| Pentadecane | 310 |
| Hexadecane | 330 |
| Heptadecane | 410 |
| Octadecane | 570 |
| Aromatics | |
| Benzene | <20 |
| Toluene | 120 |
| o-Xylene | 100 |
| m-Xylene | 170 |
| Ethylbenzene | 220 |
| iso-Propylbenzene | |
| Butylbenzene | 340 |
| Hexylbenzene | 420 |
| Heptylbenzene | 1180 |
| Octylbenzene | 450 |
| 2-Methylnaphthalene | 590 |
| Mixtures | |
| Hexadecane + 2-methylnaphthalene[a] | 360 |
| Hexadecane + 2-methylnaphthalene[b] | 950 |
| Hexadecane + 2-methylnaphthalene[c] | 1200 |
| Hexadecane + 2-methylnaphthalene[d] | 1400 |
| Cyclohexane + hexadecane[b] | 320 |
| Benzene + cyclohexane[b] | <20 |
| Toluene + cyclohexane[b] | 30 |
| Crude oil | 1900 |

[a]Ratio of 2:1, vol/vol
[b]Ratio of 1:1, vol/vol
[c]Ratio of 1:1.5, vol/vol
[d]Ratio of 1:2, vol/vol

EXAMPLE 12

The standard emulsification assay was carried out, using 20 mM Acetate buffer for the pH range 3.3–5.3 and 20 mM Tris-HCI buffer for the pH range 5.4–9.2. Activity was measured at the different pH values, with (■) and without (□) the addition of 10 mM MgSO$_4$. E-KA53 was present at a concentration of 13.3 μg/ml. The effect of pH and magnesium ions on the emulsifying activity of E-KA53 is shown in the FIGURE.

While the examples provided only exemplify working up the cell culture medium by precipitation with ammonium sulfate it will be apparent to the skilled artisan that the crude cell culture medium may also be worked up by ultrafiltration, sedimentation, centrifugation, precipitation and dialysis techniques, all of which are available to the art.

It is contemplated that the emulsifying activity of the E-KA53 will be enhanced by heating at a temperature in the range of from about 60° to 100° C.

The bioemulsifier described herein has many varied uses, as mentioned above. It can be used to stabilize oil-in-water mixtures, emulsions or dispersions, to reduce the fat content in fat-containing foodstuffs, to increase the shelf-life of a foodstuff, to improve the effectiveness or properties of pharmaceuticals, agricultural products, textile treatments, soaps, detergents, and the like, to form stable dispersions of hydrophobic materials in hydrophilic or hydrophobic solvents, and to form stable cosmetics. In each case an effective amount of bioemulsifier is added to the base material, which effective amount can vary dependent upon application. It is within the scope of the invention that addition of from about 0.001 to 10% by weight, based upon the total weight of the final product, could be effective accomplish the desired results or treatment. The potential uses of the bioemulsifier described herein includes uses for similar materials described in U.S. Pat. Nos. 5,212,235, 4,395,354, 4,883,757, 4,737,359, and 4,999,195, each of which is incorporated herein by reference. Also, conventional emulsifiers can be added as well, such as are described, for example, in said patents.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An isolated bioemulsifier designated Alasan or E-KA53 produced from *Acinetobacter radioresistens* strain KA53 and which in its essentially pure form has the following characteristics:

(a) Molecular weight from 100,000 to 2,000,000 Daltons;

(b) Emulsifying activity which increases with preheating at increasing temperatures—60°–90° C.;

(c) Resistance to strong alkali while retaining emulsifying activity;

(d) Reduced viscosity that varies as a function of temperature treatment;

(e) Emulsifying activity that varies as a function of pH and magnesium ions; and (f) Specific constituent building blocks defined in Table 4 and Table 5.

2. An isolated bioemulsifier designated APO-E-KA53 produced from bioemulsifier E-KA53 which in its essentially pure form has the following characteristics:

(a) Alanine covalently bound to a polysaccharide representing 7 percent of the total dry weight of APO-E-KA53;

(b) Acid-base titration of APO-E-KA53 showing an anionic polymer containing 1.28 micromole of carboxyl groups per milligram of APO-E-KA53 being titrated;

(c) The UV absorption spectrum of APO-E-KA53 showing a single maximum at 209 nm; and (d) The $^{13}$C-NMR of APO-E-KA53 as summarized in Table 6.

3. A process for the production of a bioemulsifier designated E-KA53 which comprises cultivating the strain *Acinetobacter radioresistens* KA53 until the bioemulsifier is obtained in the culture medium.

4. A process according to claim 3 where a crude is worked up by ultrafiltration, sedimentation, centrifugation, precipitation or dialysis.

5. A bioemulsifier in accordance with any of claims 1 or 2, wherein the bioemulsifier is heated from 60°–100° C. to obtain an activated form.

6. A method of emulsifying organic materials or hydrophobic materials, using E-KA53, wherein the bioemulsifier is in its crude or pure form, or activated form.

7. A method of emulsifying organic materials or hydrophobic materials using APO-E-KA53 or activated APO-E-KA53.

8. A method of emulsifying organic materials or hydrophobic materials selected from the group consisting of solvents, pesticides, herbicides, pigments, food and vegetable oils using a bioemulsifier in accordance with any of claims 1 or 2.

9. An isolated culture of a new microorganism designated Acinetobacter—KA53 (Accession No. NCIMB 40692).

10. A method of forming and stabilizing an oil-in-water emulsion comprising adding a bioemulsifier in accordance with claim 1 to an oil and water mixture.

11. A method of forming and stabilizing an oil-in-water emulsion comprising adding a bioemulsifier in accordance with claim 1 together with another emulsifier to an oil and water mixture.

12. A method of forming and stabilizing an oil-in-water emulsion for use in detergents, cosmetics, medicine, the food industry, the pharmaceutical industry, the textile industry, in pigments, in bioremediation, in agriculture, in pesticide formulations and in herbicide formulations comprising adding a bioemulsifier in accordance with claim 1 to an oil and water mixture.

13. A substantially pure culture of *Acinetobacter radioresistens* strain KA53.

14. A method of forming a stable oil-in-water mixture which comprises adding an effective amount of a bioemulsifier of claim 1 or 2 to an oil-in-water mixture.

15. A method of reducing the fat content of a foodstuff which comprises adding an effective amount of a bioemulsifier of claim 1 or 2 to a foodstuff being prepared.

16. A method of increasing the shelf-life of a foodstuff which comprises adding to the foodstuff an effective amount of a bioemulsifier of claim 1 or 2.

17. A method of forming a stable dispersion of hydrophobic material in a hydrophilic solvent which comprises adding an effective amount of a bioemulsifier of claim 1 or 2 to a dispersion of the hydrophobic material in the hydrophilic solvent.

18. The method of claim 17, wherein the dispersion is a dispersion of one or more herbicides, one or more pesticides, or one or more pigments in water.

19. A method of forming a stable dispersion of hydrophobic material in a hydrophobic solvent which comprises adding an effective amount of a bioemulsifier of claim 1 or 2 to a dispersion of the hydrophobic material in the hydrophobic solvent.

20. The method of claim 19, wherein the hydrophobic solvent is a petroleum product.

21. The method of claim 14 wherein one or more additional emulsifiers are added.

22. A method of forming a stable cosmetic material which comprises adding an effective amount of a bioemulsifier of claim 1 or 2 to cosmetic material.

23. A method for forming an agricultural product which comprises adding an effective amount of a bioemulsifier of claim 1 or 2 to an agricultural product.

24. The method of claim 23, wherein the agricultural product is a herbicide or pesticide.

25. A method for producing an improved textile treatment substance which comprises adding an effective amount of a bioemulsifier of claim 1 or 2 to a textile treatment substance.

26. The method of claim 25, wherein the textile treatment substance is a pigment.

27. The method of claim 15, wherein one or more additional emulsifiers are added.

28. The method of claim 16, wherein one or more additional emulsifiers are added.

29. The method of claim 17, wherein one or more additional emulsifiers are added.

30. The method of claim 19, wherein one or more additional emulsifiers are added.

* * * * *